United States Patent
Isaacson et al.

(10) Patent No.: US 12,070,605 B2
(45) Date of Patent: Aug. 27, 2024

(54) DYNAMICALLY OPTIMIZED NEURAL SENSING

(71) Applicant: Medtronic, Inc., Minneapolis, MN (US)

(72) Inventors: Benjamin P. Isaacson, Mahtomedi, MN (US); David E. Linde, Corcoran, MN (US); Scott R. Stanslaski, Shoreview, MN (US); Christopher L. Pulliam, Plymouth, MN (US); Rene A. Molina, Maple Grove, MN (US); Abbey Beuning Holt Becker, Shoreview, MN (US); David L. Carlson, Fridley, MN (US); Nicholas D. Buse, New Brighton, MN (US); Duane L. Bourget, Andover, MN (US); Thaddeus S. Brink, St. Paul, MN (US)

(73) Assignee: Medtronic, Inc., Minneapolis, MN (US)

(*) Notice: Subject to any disclaimer, the term of this patent is extended or adjusted under 35 U.S.C. 154(b) by 77 days.

(21) Appl. No.: 17/651,374

(22) Filed: Feb. 16, 2022

(65) Prior Publication Data
US 2022/0266031 A1    Aug. 25, 2022

Related U.S. Application Data

(60) Provisional application No. 63/152,912, filed on Feb. 24, 2021.

(51) Int. Cl.
*A61N 1/36* (2006.01)
*A61N 1/05* (2006.01)
*A61N 1/372* (2006.01)

(52) U.S. Cl.
CPC ....... *A61N 1/36175* (2013.01); *A61N 1/0534* (2013.01); *A61N 1/36135* (2013.01); *A61N 1/36192* (2013.01); *A61N 1/37235* (2013.01)

(58) Field of Classification Search
CPC .............. A61N 1/0534; A61N 1/36082; A61N 1/36135; A61N 1/36139; A61N 1/36175; A61N 1/36192; A61N 1/37235
See application file for complete search history.

(56) References Cited

U.S. PATENT DOCUMENTS

| | | |
|---|---|---|
| 9,586,051 B2 | 3/2017 | Greenhut et al. |
| 9,586,053 B2 | 3/2017 | Moffitt et al. |

(Continued)

FOREIGN PATENT DOCUMENTS

WO    2019164952 A1    8/2019

OTHER PUBLICATIONS

Herron et al., "Chronic electrocorticography for sensing movement intention and closed-loop deep brain stimulation with wearable sensors in an essential tremor patient", Journal of Neurosurgery, vol. 127, No. 3, Nov. 18, 2016, pp. 580-587, https://doi.org/10.3171/2016.8.JNS16536.

(Continued)

*Primary Examiner* — Amanda K Hulbert
(74) *Attorney, Agent, or Firm* — Shumaker & Sieffert, P.A.

(57) ABSTRACT

An example method includes determining, by an implantable medical device (IMD), an electrode of a plurality of electrodes of a lead to be used to deliver electrical stimulation to a patient at a particular time; selecting, by the IMD and based on the determined electrode, a set of electrodes of the plurality of electrodes; and sensing, by the IMD and via the selected set of electrodes, electrical signals of the patient at the particular time.

16 Claims, 9 Drawing Sheets

(56) References Cited

U.S. PATENT DOCUMENTS

| | | |
|---|---|---|
| 2007/0288076 A1 | 12/2007 | Bulkes et al. |
| 2012/0053658 A1* | 3/2012 | Gabriela .............. A61N 1/0534 607/62 |
| 2012/0109257 A1 | 5/2012 | Yoo et al. |
| 2013/0165998 A1 | 6/2013 | Libbus et al. |
| 2019/0022397 A1 | 1/2019 | Srivastava et al. |
| 2020/0306543 A1 | 10/2020 | Boor et al. |

OTHER PUBLICATIONS

Extended Search Report from counterpart European Application No. 22158605.0, dated Jul. 12, 2022, p. 6.

Response to Extended Search Report dated Jul. 11, 2022, from counterpart European Application No. 22158605.0 filed Feb. 14, 2023, 13 pp.

* cited by examiner

DYNAMICALLY OPTIMIZED NEURAL SENSING

This application claims the benefit of U.S. Provisional Patent Application No. 63/152,912, filed 24 Feb. 2021, the entire contents of which is incorporated herein by reference.

TECHNICAL FIELD

This disclosure generally relates to electrical stimulation and recording.

BACKGROUND

Medical devices may be external or implanted, and may be used to deliver electrical stimulation therapy to various tissue sites of a patient to treat a variety of symptoms or conditions such as chronic pain, tremor, Parkinson's disease, other movement disorders, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Hence, electrical stimulation may be used in different therapeutic applications, such as deep brain stimulation (DBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes for delivery of the stimulation, a polarity of each selected electrode, a voltage or current amplitude, a pulse width, and a pulse frequency as stimulation parameters. A set of parameters, such as a set including electrode combination, electrode polarity, voltage or current amplitude, pulse width and pulse rate, may be referred to as a program in the sense that they define the electrical stimulation therapy to be delivered to the patient.

DETAILED DESCRIPTION

In general, the disclosure describes devices, systems, and techniques for dynamic neural sensing by an implantable medical device (IMD). Sensed electrical signals can serve as control signals for electrical stimulation therapies. Some electrical stimulation patterns (e.g., largely continuous tonic stimulation) may allow for relatively straightforward ways to embed sensing periods. As electrical stimulation concepts and forms become more complex (e.g., in terms of varying parameters and attributes), the ability to sense electrical signals becomes more challenging due to the increased number of interactions between stimulation parameters and sensing parameters, as well as the fact that the interactions may not be static over time.

In accordance with one or more techniques of this disclosure, as opposed to using a static sensing pattern, an IMD may use a dynamic sensing pattern. For instance, the IMD may dynamically determine when to perform sensing and/or dynamically determine which electrodes to utilize for the sensing. As one example, the IMD may determine which electrodes of a plurality of electrodes to utilize for sensing at a particular time based on which of the plurality of electrodes are to be used to deliver stimulation at the particular time (e.g., the IMD may select sensing electrodes that "sandwich" a stimulation electrode). The IMD may determine whether to perform sensing during delivery of stimulation (e.g., sense in parallel with stimulation delivery), to perform sensing when stimulation is not being delivered, or to perform sensing both during delivery of stimulation and when stimulation is not being delivered. The IMD may "tag" or otherwise mark which sense data was measured during stimulation delivery and which was not.

The IMD may perform closed-loop stimulation based on results of the sensing. The IMD may utilize either all of the sensing data or a sub-set of the sensing data. As one example, the IMD may not perform closed-loop stimulation based on sensing data measured while stimulation is being delivered. For instance, the IMD may blank inputs to the closed-loop algorithm during stimulation delivery. As another example, the IMD may perform closed-loop stimulation based on both sensing data measured while stimulation is being delivered.

Although this disclosure is directed to DBS therapy, the systems, devices, and techniques described herein may similarly detect movement of leads and electrodes implanted outside of the brain, such as near other nerves or muscles for different diagnostic or therapeutic applications, such as spinal cord stimulation (SCS), pelvic stimulation, gastric stimulation, or peripheral nerve field stimulation (PNFS). Moreover, a human patient is described for example purposes herein, but similar systems, devices, and techniques may be used for other animals in other examples.

Figure 1:
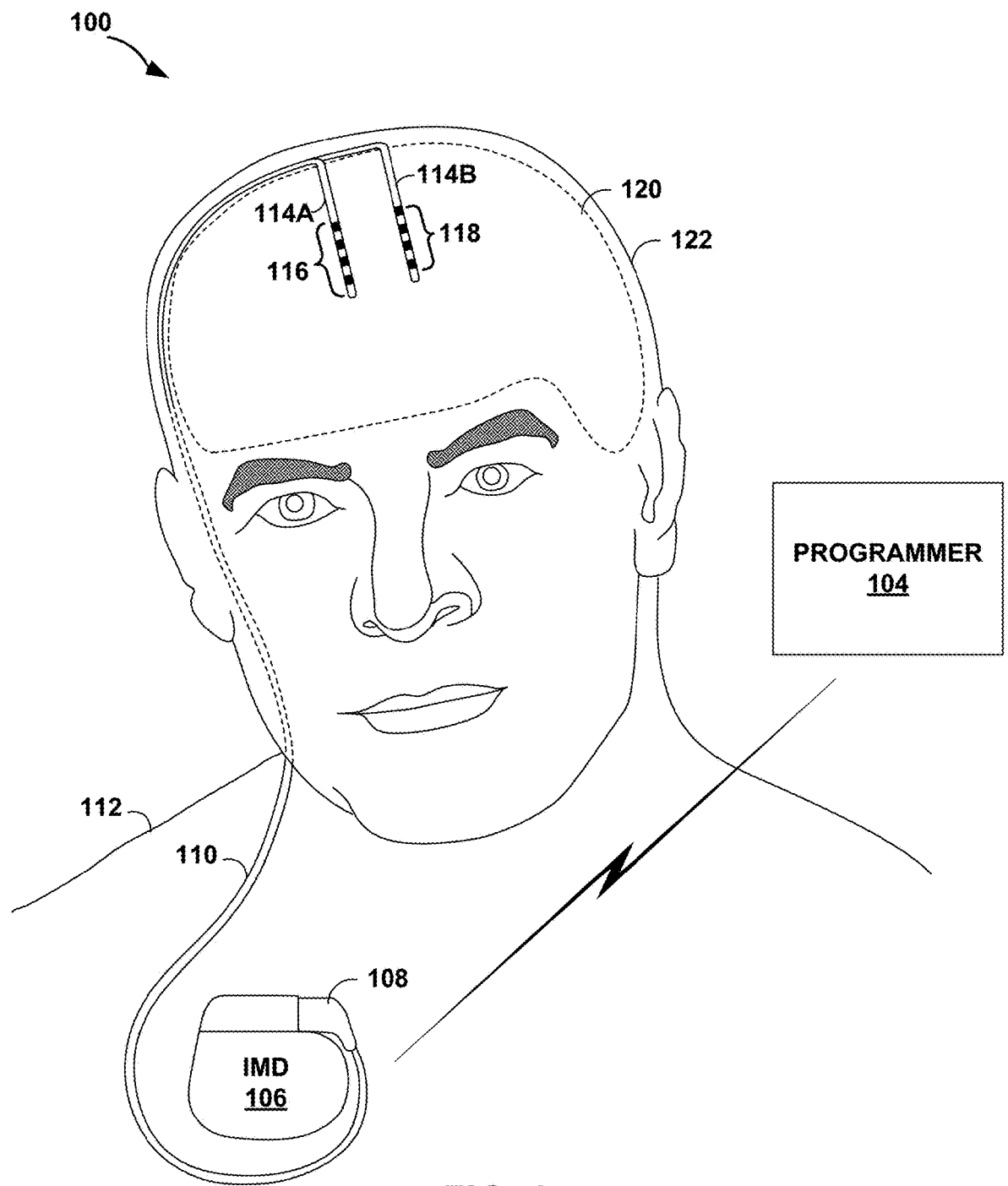
FIG. 1 is a conceptual diagram illustrating an example system that includes an implantable medical device (IMD) configured to deliver deep brain stimulation (DBS) to a patient according to an example of the techniques of the disclosure.

FIG. 1 is a conceptual diagram illustrating an example system 100 that includes an implantable medical device (IMD) 106 configured to deliver DBS to patient 122 according to an example of the techniques of the disclosure. As shown in the example of FIG. 1, example system 100 includes medical device programmer 104, implantable medical device (IMD) 106, lead extension 110, and leads 114A and 114B with respective sets of electrodes 116, 118. In the example shown in FIG. 1, electrodes 116, 118 of leads 114A, 114B are positioned to deliver electrical stimulation to a tissue site within brain 120, such as a deep brain site under the dura mater of brain 120 of patient 112. In some examples, delivery of stimulation to one or more regions of brain 120, such as the subthalamic nucleus, globus pallidus or thalamus, may be an effective treatment to manage movement disorders, such as Parkinson's disease. Some or all of electrodes 116, 118 also may be positioned to sense neurological brain signals within brain 120 of patient 112. In some examples, some of electrodes 116, 118 may be configured to sense neurological brain signals and others of electrodes 116, 118 may be configured to deliver adaptive electrical stimulation to brain 120. In other examples, all of electrodes 116, 118 are configured to both sense neurological brain signals and deliver adaptive electrical stimulation to brain 120.

IMD 106 includes a therapy module (e.g., which may include processing circuitry, signal generation circuitry or other electrical circuitry configured to perform the functions attributed to IMD 106) that includes a stimulation generator configured to generate and deliver electrical stimulation therapy to patient 112 via a subset of electrodes 116, 118 of leads 114A and 114B, respectively. The subset of electrodes 116, 118 that are used to deliver electrical stimulation to patient 112, and, in some cases, the polarity of the subset of electrodes 116, 118, may be referred to as a stimulation electrode combination. As described in further detail below, the stimulation electrode combination can be selected for a particular patient 112 and target tissue site (e.g., selected based on the patient condition). The group of electrodes 116, 118 includes at least one electrode and can include a plurality of electrodes. In some examples, the plurality of electrodes 116 and/or 118 may have a complex electrode geometry such that two or more electrodes of the lead are located at different positions around the perimeter of the respective lead (e.g., different positions around a longitudinal axis of the lead).

In some examples, the neurological signals (e.g., an example type of electrical signals) sensed within brain 120 may reflect changes in electrical current produced by the sum of electrical potential differences across brain tissue. Examples of neurological brain signals include, but are not limited to, electrical signals generated from local field potentials (LFP) sensed within one or more regions of brain 120, such as an electroencephalogram (EEG) signal, or an electrocorticogram (ECoG) signal. Local field potentials, however, may include a broader genus of electrical signals within brain 120 of patient 112.

In some examples, the neurological brain signals that are used to select a stimulation electrode combination may be sensed within the same region of brain 120 as the target tissue site for the electrical stimulation. As previously indicated, these tissue sites may include tissue sites within anatomical structures such as the thalamus, subthalamic nucleus or globus pallidus of brain 120, as well as other target tissue sites. The specific target tissue sites and/or regions within brain 120 may be selected based on the patient condition. Thus, due to these differences in target locations, in some examples, the electrodes used for delivering electrical stimulation may be different than the electrodes used for sensing neurological brain signals. In other examples, the same electrodes may be used to deliver electrical stimulation and sense brain signals. However, this configuration would require the system to switch between stimulation generation and sensing circuitry and may reduce the time the system can sense brain signals.

Electrical stimulation generated by IMD 106 may be configured to manage a variety of disorders and conditions. In some examples, the stimulation generator of IMD 106 is configured to generate and deliver electrical stimulation pulses to patient 112 via electrodes of a selected stimulation electrode combination. However, in other examples, the stimulation generator of IMD 106 may be configured to generate and deliver a continuous wave signal, e.g., a sine wave or triangle wave. In either case, a stimulation generator within IMD 106 may generate the electrical stimulation therapy for DBS according to a therapy program that is selected at that given time in therapy. In examples in which IMD 106 delivers electrical stimulation in the form of stimulation pulses, a therapy program may include a set of therapy parameter values (e.g., stimulation parameters), such as a stimulation electrode combination for delivering stimulation to patient 112, pulse frequency, pulse width, and a current or voltage amplitude of the pulses. As previously indicated, the electrode combination may indicate the specific electrodes 116, 118 that are selected to deliver stimulation signals to tissue of patient 112 and the respective polarities of the selected electrodes. IMD 106 may deliver electrical stimulation intended to contribute to a therapeutic effect. In some examples, IMD 106 may also, or alternatively, deliver electrical stimulation intended to be sensed by other electrode and/or elicit a physiological response, such as an evoked compound action potential (ECAP), that can be sensed by electrodes.

IMD 106 may be implanted within a subcutaneous pocket above the clavicle, or, alternatively, on or within cranium 122 or at any other suitable site within patient 112. Generally, IMD 106 is constructed of a biocompatible material that resists corrosion and degradation from bodily fluids. IMD 106 may comprise a hermetic housing to substantially enclose components, such as a processor, therapy module, and memory.

Figure 4A:
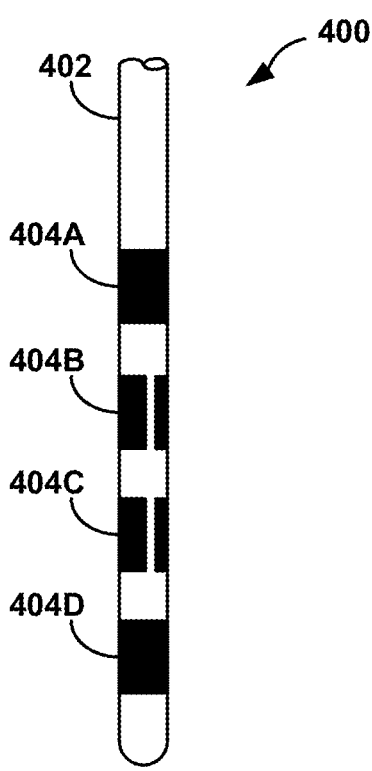
FIGS. 4A and 4B are conceptual diagrams of example leads with respective electrodes carried by the lead.
Figure 4B:
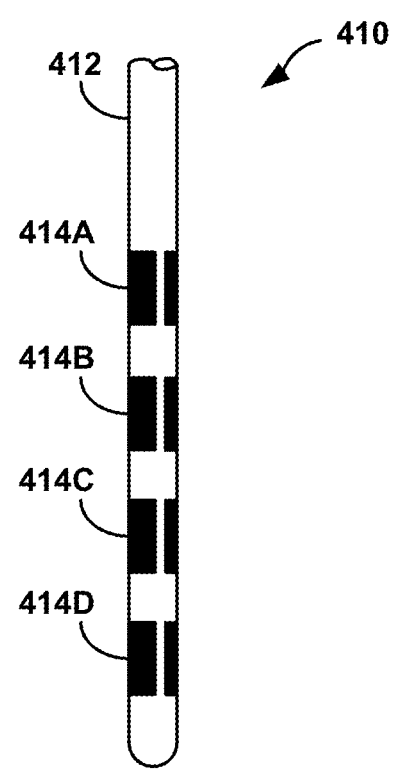

As shown in FIG. 1, implanted lead extension 110 is coupled to IMD 106 via connector 108 (also referred to as a connector block or a header of IMD 106). In the example of FIG. 1, lead extension 110 traverses from the implant site of IMD 106 and along the neck of patient 112 to cranium 122 of patient 112 to access brain 120. In the example shown in FIG. 1, leads 114A and 114B (collectively "leads 114") are implanted within the right and left hemispheres, respectively, of patient 112 in order deliver electrical stimulation to one or more regions of brain 120, which may be selected based on the patient condition or disorder controlled by therapy system 100. The specific target tissue site and the stimulation electrodes used to deliver stimulation to the target tissue site, however, may be selected, e.g., according to the identified patient behaviors and/or other sensed patient parameters. Other lead 114 and IMD 106 implant sites are contemplated. For example, IMD 106 may be implanted on or within cranium 122, in some examples. Or leads 114 may be implanted within the same hemisphere or IMD 106 may be coupled to a single lead implanted in a single hemisphere. Although leads 114 may have ring electrodes at different longitudinal positions as shown in FIG. 1, leads 114 may have electrodes disposed at different positions around the perimeter of the lead (e.g., different circumferential positions for a cylindrical shaped lead) as shown in the examples of FIGS. 4A and 4B.

Leads 114 illustrate an example lead set that include axial leads carrying ring electrodes disposed at different axial positions (or longitudinal positions). In other examples, leads may be referred to as "paddle" leads carrying planar arrays of electrodes on one side of the lead structure. In addition, as described herein, complex lead array geometries may be used in which electrodes are disposed at different respective longitudinal positions and different positions around the perimeter of the lead.

Although leads 114 are shown in FIG. 1 as being coupled to a common lead extension 110, in other examples, leads 114 may be coupled to IMD 106 via separate lead extensions or directly to connector 108. Leads 114 may be positioned to deliver electrical stimulation to one or more target tissue sites within brain 120 to manage patient symptoms associated with a movement disorder of patient 112. Leads 114 may be implanted to position electrodes 116, 118 at desired locations of brain 120 through respective holes in cranium 122. Leads 114 may be placed at any location within brain 120 such that electrodes 116, 118 are capable of providing electrical stimulation to target tissue sites within brain 120 during treatment. For example, electrodes 116, 118 may be surgically implanted under the dura mater of brain 120 or within the cerebral cortex of brain 120 via a burr hole in cranium 122 of patient 112, and electrically coupled to IMD 106 via one or more leads 114.

In the example shown in FIG. 1, electrodes 116, 118 of leads 114 are shown as ring electrodes. Ring electrodes may be used in DBS applications because ring electrodes are relatively simple to program and are capable of delivering an electrical field to any tissue adjacent to electrodes 116, 118. In other examples, electrodes 116, 118 may have different configurations. For example, in some examples, at least some of the electrodes 116, 118 of leads 114 may have a complex electrode array geometry that is capable of producing shaped electrical fields. The complex electrode array geometry may include multiple electrodes (e.g., partial ring or segmented electrodes) around the outer perimeter of each lead 114, rather than one ring electrode, such as shown in FIGS. 4A and 4B. In this manner, electrical stimulation may be directed in a specific direction from leads 114 to enhance therapy efficacy and reduce possible adverse side effects from stimulating a large volume of tissue. In some examples, a housing of IMD 106 may include one or more stimulation and/or sensing electrodes. In alternative examples, leads 114 may have shapes other than elongated cylinders as shown in FIG. 1. For example, leads 114 may be paddle leads, spherical leads, bendable leads, or any other type of shape effective in treating patient 112 and/or minimizing invasiveness of leads 114.

In the example shown in FIG. 1, IMD 106 includes a memory to store a plurality of therapy programs that each define a set of therapy parameter values. In some examples, IMD 106 may select a therapy program from the memory based on various parameters, such as sensed patient parameters and the identified patient behaviors. IMD 106 may generate electrical stimulation based on the selected therapy program to manage the patient symptoms associated with a movement disorder.

External programmer 104 wirelessly communicates with IMD 106 as needed to provide or retrieve therapy information. Programmer 104 is an external computing device that the user, e.g., a clinician and/or patient 112, may use to communicate with IMD 106. For example, programmer 104 may be a clinician programmer that the clinician uses to communicate with IMD 106 and program one or more therapy programs for IMD 106. Alternatively, programmer 104 may be a patient programmer that allows patient 112 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 106. Programmer 104 may enter a new programming session for the user to select new stimulation parameters for subsequent therapy.

When programmer 104 is configured for use by the clinician, programmer 104 may be used to transmit initial programming information to IMD 106. This initial information may include hardware information, such as the type of leads 114 and the electrode arrangement, the position of leads 114 within brain 120, the configuration of electrode array 116, 118, initial programs defining therapy parameter values, and any other information the clinician desires to program into IMD 106. Programmer 104 may also be capable of completing functional tests (e.g., measuring the impedance of electrodes 116, 118 of leads 114). In some examples, programmer 104 may receive sensed signals or representative information and perform the same techniques and functions attributed to IMD 106 herein. In other examples, a remote server (e.g., a standalone server or part of a cloud service) may perform the functions attributed to IMD 106, programmer 104, or any other devices described herein.

The clinician may also store therapy programs within IMD 106 with the aid of programmer 104. During a programming session, the clinician may determine one or more therapy programs that may provide efficacious therapy to patient 112 to address symptoms associated with the patient condition, and, in some cases, specific to one or more different patient states, such as a sleep state, movement state or rest state. For example, the clinician may select one or more stimulation electrode combination with which stimulation is delivered to brain 120. During the programming session, the clinician may evaluate the efficacy of the specific program being evaluated based on feedback provided by patient 112 or based on one or more physiological parameters of patient 112 (e.g., muscle activity, muscle tone, rigidity, tremor, etc.). Alternatively, identified patient behavior from video information may be used as feedback during the initial and subsequent programming sessions. Programmer 104 may assist the clinician in the creation/identification of therapy programs by providing a methodical system for identifying potentially beneficial therapy parameter values.

Programmer 104 may also be configured for use by patient 112. When configured as a patient programmer, programmer 104 may have limited functionality (compared to a clinician programmer) in order to prevent patient 112 from altering critical functions of IMD 106 or applications that may be detrimental to patient 112. In this manner, programmer 104 may only allow patient 112 to adjust values for certain therapy parameters or set an available range of values for a particular therapy parameter.

Programmer 104 may also provide an indication to patient 112 when therapy is being delivered, when patient input has triggered a change in therapy or when the power source within programmer 104 or IMD 106 needs to be replaced or recharged. For example, programmer 112 may include an alert LED, may flash a message to patient 112 via a programmer display, generate an audible sound or somatosensory cue to confirm patient input was received, e.g., to indicate a patient state or to manually modify a therapy parameter.

Therapy system 100 may be implemented to provide chronic stimulation therapy to patient 112 over the course of several months or years. However, system 100 may also be employed on a trial basis to evaluate therapy before committing to full implantation. If implemented temporarily, some components of system 100 may not be implanted within patient 112. For example, patient 112 may be fitted with an external medical device, such as a trial stimulator, rather than IMD 106. The external medical device may be coupled to percutaneous leads or to implanted leads via a percutaneous extension. If the trial stimulator indicates DBS system 100 provides effective treatment to patient 112, the clinician may implant a chronic stimulator within patient 112 for relatively long-term treatment.

Although IMD 106 is described as delivering electrical stimulation therapy to brain 120, IMD 106 may be configured to direct electrical stimulation to other anatomical regions of patient 112 in other examples. In other examples, system 100 may include an implantable drug pump in addition to, or in place of, IMD 106. Further, an IMD may provide other electrical stimulation such as spinal cord stimulation to treat a movement disorder.

As discussed above, IMD 106 may sense neurological signals (e.g., electrical signals) of patient 112. For instance, circuitry of IMD 106 may sense a differential voltage level across two electrodes of leads 114. IMD 106 may utilize the sensed electrical signals as control signals for electrical stimulation therapies. Some electrical stimulation patterns (e.g., largely continuous tonic stimulation) may allow for relatively straightforward ways to embed sensing periods. As electrical stimulation concepts and forms become more complex (e.g., in terms of varying parameters and attributes), the ability to sense electrical signals becomes more challenging due to the increased number of interactions between stimulation parameters and sensing parameters, as well as the fact that the interactions may not be static over time.

In accordance with one or more techniques of this disclosure, as opposed to using a static sensing pattern, IMD 106 may use a dynamic sensing pattern. For instance, IMD 106 may dynamically determine when to perform sensing and/or dynamically determine which electrodes to utilize for the sensing. As one example, IMD 106 may determine which electrodes of electrodes 116, 118 to utilize for sensing at a particular time based on which of electrodes of electrodes 116, 118 are to be used to deliver stimulation at the particular time (e.g., IMD 106 may select sensing electrodes that "sandwich" a stimulation electrode). IMD 106 may determine whether to perform sensing during delivery of stimulation (e.g., sense in parallel with stimulation delivery), to perform sensing when stimulation is not being delivered, or to perform sensing both during delivery of stimulation and when stimulation is not being delivered.

Utilizing a dynamic sensing pattern may present one or more advantages. As one example, by having IMD 106 dynamically determine when to perform sensing and/or dynamically determine which electrodes to utilize for the sensing, IMD 106 may be able to maintain sensing capabilities (e.g., regardless of simulation complexity). As another example, by having IMD 106 dynamically determine when to perform sensing and/or dynamically determine which electrodes to utilize for the sensing, the programming burden may be reduced (e.g., as sensing windows and/or electrodes may not have to be explicitly programmed).

The architecture of system 100 illustrated in FIG. 1 is shown as an example. The techniques as set forth in this disclosure may be implemented in the example system 100 of FIG. 1, as well as other types of systems not described specifically herein. Nothing in this disclosure should be construed so as to limit the techniques of this disclosure to the example architecture illustrated by FIG. 1.

Figure 2:
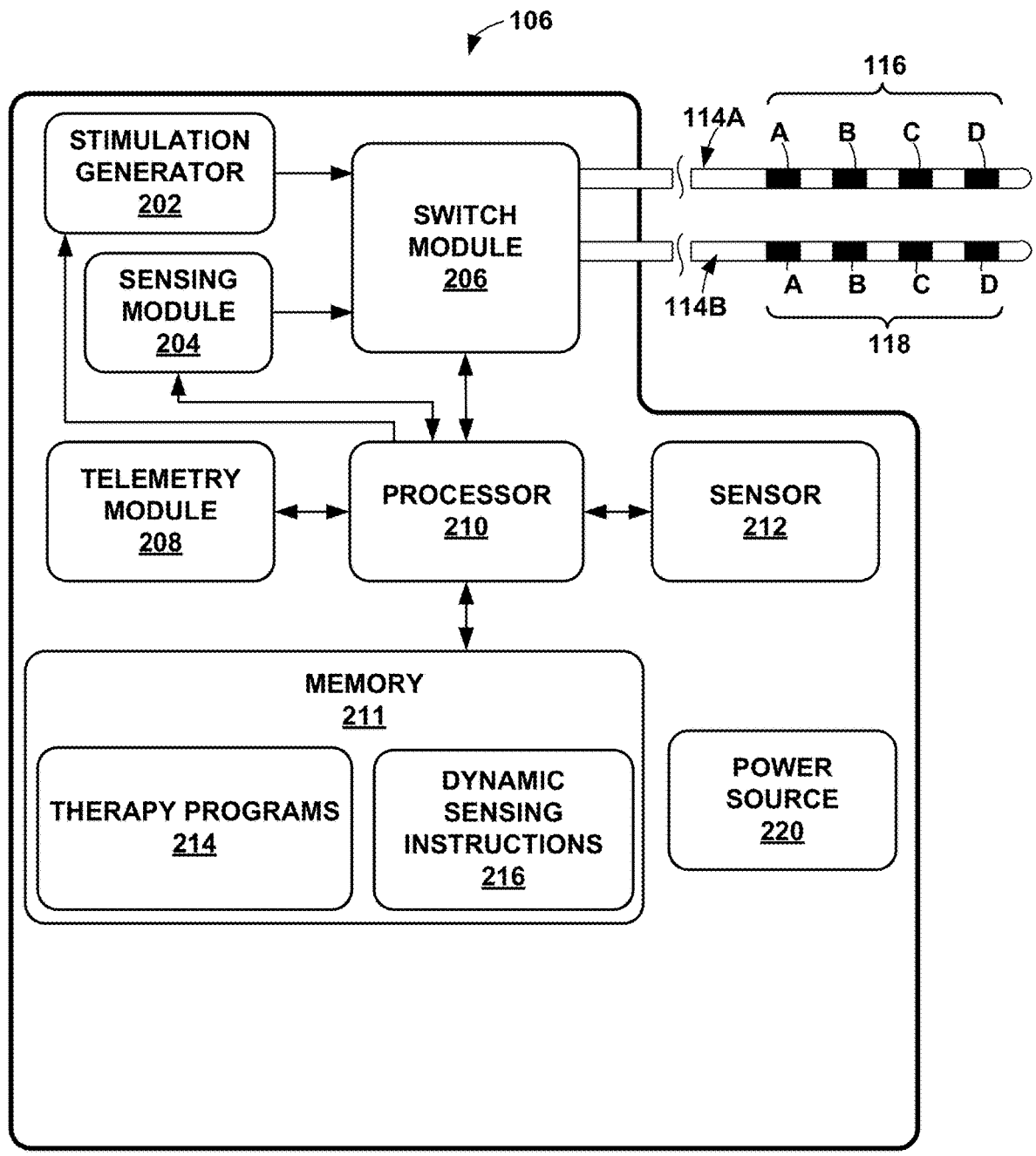
FIG. 2 is a block diagram of the example IMD of FIG. 1 for delivering DBS therapy according to an example of the techniques of the disclosure.

FIG. 2 is a block diagram of the example IMD 106 of FIG. 1 for delivering DBS therapy. In the example shown in FIG. 2, IMD 106 includes processor 210, memory 211, stimulation generator 202, sensing module 204, switch module 206, telemetry module 208, sensor 212, and power source 220. Each of these modules may be or include electrical circuitry configured to perform the functions attributed to each respective module. For example, processor 210 may include processing circuitry, switch module 206 may include switch circuitry, sensing module 204 may include sensing circuitry, and telemetry module 208 may include telemetry circuitry. Switch module 204 may not be necessary for multiple current source and sink configurations. Memory 211 may include any volatile or non-volatile media, such as a random-access memory (RAM), read only memory (ROM), non-volatile RAM (NVRAM), electrically erasable programmable ROM (EEPROM), flash memory, and the like. Memory 211 may store computer-readable instructions that, when executed by processor 210, cause IMD 106 to perform various functions. Memory 211 may be a storage device or other non-transitory medium.

In the example shown in FIG. 2, memory 211 stores therapy programs 214 that include respective stimulation parameter sets that define therapy. Each stored therapy program 214 defines a particular set of electrical stimulation parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis. Memory 211 may also include dynamic sensing instructions 216 that define the process by which processor 210 dynamically determines when to perform sensing and/or dynamically determines which electrodes to utilize for the sensing.

Stimulation generator 202, under the control of processor 210, generates stimulation signals for delivery to patient 112 via selected combinations of electrodes 116, 118. An example range of electrical stimulation parameters believed to be effective in DBS to manage a movement disorder of patient include:

1. Pulse Rate, i.e., Frequency: between approximately 0.1 Hertz and approximately 500 Hertz, such as between approximately 0.1 to 10 Hertz, approximately 40 to 185 Hertz, or such as approximately 140 Hertz.
2. In the case of a voltage controlled system, Voltage Amplitude: between approximately 0.1 volts and approximately 50 volts, such as between approximately 2 volts and approximately 3 volts.
3. In the alternative case of a current controlled system, Current Amplitude: between approximately 0.2 milliamps to approximately 100 milliamps, such as between approximately 1.3 milliamps and approximately 2.0 milliamps.
4. Pulse Width: between approximately 10 microseconds and approximately 5000 microseconds, such as between approximately 100 microseconds and approximately 1000 microseconds, or between approximately 180 microseconds and approximately 450 microseconds.

Accordingly, in some examples, stimulation generator 202 generates electrical stimulation signals in accordance with the electrical stimulation parameters noted above. Other ranges of therapy parameter values may also be useful, and may depend on the target stimulation site within patient 112. While stimulation pulses are described, stimulation signals may be of any form, such as continuous-time signals (e.g., sine waves) or the like. Stimulation signals configured to elicit ECAPs or other evoked physiological signals may be similar or different from the above parameter value ranges.

Processor 210 may include fixed function processing circuitry and/or programmable processing circuitry, and may comprise, for example, any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processor 210 herein may be embodied as firmware, hardware, software or any combination thereof. Processor 210 may control stimulation generator 202 according to therapy programs 214 stored in memory 211 to apply particular stimulation parameter values specified by one or more of programs, such as voltage amplitude or current amplitude, pulse width, or pulse rate.

In the example shown in FIG. 2, the set of electrodes 116 includes electrodes 116A, 116B, 116C, and 116D, and the set of electrodes 118 includes electrodes 118A, 118B, 118C, and 118D. Processor 210 also controls switch module 206 to apply the stimulation signals generated by stimulation generator 202 to selected combinations of electrodes 116, 118. In particular, switch module 204 may couple stimulation signals to selected conductors within leads 114, which, in turn, deliver the stimulation signals across selected electrodes 116, 118. Switch module 206 may be a switch array, switch matrix, multiplexer, or any other type of switching module configured to selectively couple stimulation energy to selected electrodes 116, 118 and to selectively sense neurological brain signals with selected electrodes 116, 118. Hence, stimulation generator 202 is coupled to electrodes 116, 118 via switch module 206 and conductors within leads 114. In some examples, however, IMD 106 does not include switch module 206.

Stimulation generator 202 may be a single channel or multi-channel stimulation generator. In particular, stimulation generator 202 may be capable of delivering a single stimulation pulse, multiple stimulation pulses, or a continuous signal at a given time via a single electrode combination or multiple stimulation pulses at a given time via multiple electrode combinations. In some examples, however, stimulation generator 202 and switch module 206 may be configured to deliver multiple channels on a time-interleaved basis. For example, switch module 206 may serve to time divide the output of stimulation generator 202 across different electrode combinations at different times to deliver multiple programs or channels of stimulation energy to patient 112. Alternatively, stimulation generator 202 may comprise multiple voltage or current sources and sinks that are coupled to respective electrodes to drive the electrodes as cathodes or anodes. In this example, IMD 106 may not require the functionality of switch module 206 for time-interleaved multiplexing of stimulation via different electrodes.

Electrodes 116, 118 on respective leads 114 may be constructed of a variety of different designs. For example, one or both of leads 114 may include two or more electrodes at each longitudinal location along the length of the lead, such as multiple electrodes at different perimeter locations around the perimeter of the lead at each of the locations A, B, C, and D. On one example, the electrodes may be electrically coupled to switch module 206 via respective wires that are straight or coiled within the housing the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 114. These and other constructions may be used to create a lead with a complex electrode geometry.

Although sensing module 204 is incorporated into a common housing with stimulation generator 202 and processor 210 in FIG. 2, in other examples, sensing module 204 may be in a separate housing from IMD 106 and may communicate with processor 210 via wired or wireless communication techniques. Example neurological brain signals include, but are not limited to, a signal generated from local field potentials (LFPs) within one or more regions of brain 28. EEG and ECoG signals are examples of local field potentials that may be measured within brain 120. However, local field potentials may include a broader genus of electrical signals within brain 120 of patient 112. Instead of, or in addition to, LFPs, IMD 106 may be configured to detect patterns of single-unit activity and/or multi-unit activity. IMD 106 may sample this activity at rates above 1,000 Hz, and in some examples within a frequency range of 6,000 Hz to 40,000 Hz. IMD 106 may identify the wave-shape of single units and/or an envelope of unit modulation that may be features used to differentiate or rank electrodes. In some examples, this technique may include phase-amplitude coupling to the envelope or to specific frequency bands in the LFPs sensed from the same or different electrodes.

Sensor 212 may include one or more sensing elements that sense values of a respective patient parameter. For example, sensor 212 may include one or more accelerometers, optical sensors, chemical sensors, temperature sensors, pressure sensors, or any other types of sensors. Sensor 212 may output patient parameter values that may be used as feedback to control delivery of therapy. IMD 106 may include additional sensors within the housing of IMD 106 and/or coupled via one of leads 114 or other leads. In addition, IMD 106 may receive sensor signals wirelessly from remote sensors via telemetry module 208, for example. In some examples, one or more of these remote sensors may be external to patient (e.g., carried on the external surface of the skin, attached to clothing, or otherwise positioned external to the patient).

Telemetry module 208 supports wireless communication between IMD 106 and an external programmer 104 or another computing device under the control of processor 210. Processor 210 of IMD 106 may receive, as updates to programs, values for various stimulation parameters such as magnitude and electrode combination, from programmer 104 via telemetry module 208. The updates to the therapy programs may be stored within therapy programs 214 portion of memory 211. In addition, processor 210 may control telemetry module 208 to transmit alerts or other information to programmer 104 that indicate a lead moved with respect to tissue. Telemetry module 208 in IMD 106, as well as telemetry modules in other devices and systems described herein, such as programmer 104, may accomplish communication by radiofrequency (RF) communication techniques. In addition, telemetry module 208 may communicate with external medical device programmer 104 via proximal inductive interaction of IMD 106 with programmer 104.

Accordingly, telemetry module 208 may send information to external programmer 104 on a continuous basis, at periodic intervals, or upon request from IMD 106 or programmer 104.

Power source 220 delivers operating power to various components of IMD 106. Power source 220 may include a small rechargeable or non-rechargeable battery and a power generation circuit to produce the operating power. Recharging may be accomplished through proximal inductive interaction between an external charger and an inductive charging coil within IMD 220. In some examples, power requirements may be small enough to allow IMD 220 to utilize patient motion and implement a kinetic energy-scavenging device to trickle charge a rechargeable battery. In other examples, traditional batteries may be used for a limited period of time.

According to the techniques of the disclosure, processor 210 of IMD 106 delivers, via electrodes 116, 118 interposed along leads 114 (and optionally switch module 206), electrical stimulation therapy to patient 112. The DBS therapy is defined by one or more therapy programs 214 having one or more parameters stored within memory 211. For example, the one or more parameters include a current amplitude (for a current-controlled system) or a voltage amplitude (for a voltage-controlled system), a pulse rate or frequency, and a pulse width, or quantity of pulses per cycle. In examples where the electrical stimulation is delivered according to a "burst" of pulses, or a series of electrical pulses defined by an "on-time" and an "off-time," the one or more parameters may further define one or more of a number of pulses per burst, an on-time, and an off-time.

As noted above, sensing module 204 may sense electrical signals via switch module 206 and electrodes of leads 114. However, in some circumstances, delivery of electrical stimulation (e.g., by stimulation generator 202 via switch module and electrodes of leads 114) may introduce artifacts, referred to as stimulation artifacts, in the sensed electrical signals. In particular, stimulation artifacts may be instructed by new simulation patterns and/or complex parameter swaps. In general, it may be desirable for IMD 106 to mitigate the impact of stimulation artifacts.

In addition to the desire to mitigate stimulation artifacts, other aspects may complicate the sensing of electrical signals. As one example, timing constraints (e.g., continuous firmware management of stimulation, and/or data acquisition and transmission) may complicate the sensing of electrical signals. As another example, hardware constraints (e.g., amplifier timing, signal processing latency, and/or telemetry latency) may complicate the sensing of electrical signals.

Memory 211 may also include dynamic sensing instructions 216 that define the process by which processor 210 dynamically determines when to perform sensing and/or dynamically determines which electrodes to utilize for the sensing. Processor 210 may cause sensing module 204 to perform sensing at the determined times and/or using the determined electrodes. By dynamically sensing in this way, IMD 106 may enable neurophysiological data to be collected more reliably and with more optimal fidelity even during delivery of complex stimulation patterns.

Dynamic sensing instructions 216 may perform the dynamic sensing in accordance with various parameters. Some example parameters follow.

As a first example parameter, if IMD 106 is delivering stimulation via a particular electrode (e.g., an electrode at position B of lead 114A), dynamic sensing instructions 216 may cause processor 210 to determine to sense electrical signals via electrodes that are symmetrically distributed across the particular electrode (e.g., an electrode at position A of lead 114A and an electrode at position C of lead 114A). In some examples, dynamic sensing instructions 216 may include instructions that cause processor 210 to wait a specified period of time after commencement of stimulation delivery until commencing to sense electrical signals (and/or mark electrical signals measured prior to an end of the specified period as non-viable and mark electrical signals measured after the end of the specified period as viable).

As a second example parameter, if IMD 106 is cycling delivery of stimulation, dynamic sensing instructions 216 may cause processor 210 to perform sensing during off-cycling periods (e.g., sense windows during which IMD 106 does not deliver electrical stimulation). In some examples, dynamic sensing instructions 216 may include instructions that cause processor 210 to wait a specified period of time after commencement of the sense window (e.g., a specified period after cessation of delivery of electrical stimulation) until commencing to sense electrical signals (and/or mark electrical signals measured prior to an end of the specified period as non-viable and mark electrical signals measured after the end of the specified period as viable). In some examples, the period of time may be dynamic. For instance, dynamic sensing instructions 216 may dynamically adjust the period of time based on a stimulation amplitude (e.g., adjust a delay of a sense window based on a determined amplitude). Longer periods of time may follow higher amplitudes and vice versa. In this way, dynamic sensing instructions 216 may reduce an amount of unreliable (e.g., invalid) sensing data acquired.

As a third example parameter, dynamic sensing instructions 216 may cause processor 210 to mark electrical signals sensed via a particular electrode as non-viable if stimulation was actively being delivered via the particular electrode while the electrical signals were sensed. In other words, sensed data (e.g., representing electrical signals) may be marked as non-valid if IMD 106 is actively delivering stimulation on sensing contacts.

As a fourth example parameter, dynamic sensing instructions 216 may cause processor 210 to embed markers/tags/labels/etc. into sensed data to indicate various events and/or to indicate when each stimulation pulse occurred. Example events include on/off, parameter switching, etc.

Dynamic sensing instructions 216 may implement any combination of the aforementioned parameters, as well as various other parameters.

Figure 3:
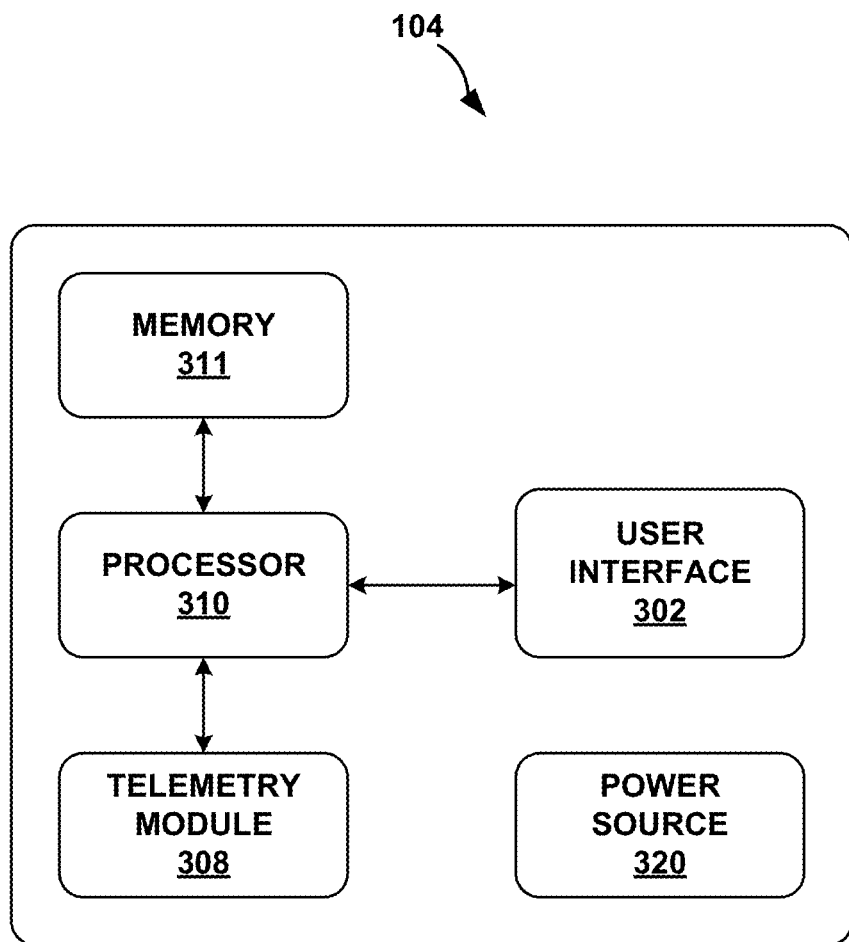
FIG. 3 is a block diagram of the external programmer of FIG. 1 for controlling delivery of DBS therapy according to an example of the techniques of the disclosure.

FIG. 3 is a block diagram of the external programmer 104 of FIG. 1 for controlling delivery of DBS therapy according to an example of the techniques of the disclosure. Although programmer 104 may generally be described as a hand-held device, programmer 104 may be a larger portable device or a more stationary device. In some examples, programmer 104 may be referred to as a tablet computing device. In addition, in other examples, programmer 104 may be included as part of a bed-side monitor, an external charging device or include the functionality of an external charging device. As illustrated in FIG. 3, programmer 104 may include a processor 310, memory 311, user interface 302, telemetry module 308, and power source 320. Memory 311 may store instructions that, when executed by processor 310, cause processor 310 and external programmer 104 to provide the functionality ascribed to external programmer 104 throughout this disclosure. Each of these components, or modules, may include electrical circuitry that is configured to perform some or all of the functionality described herein.

For example, processor 310 may include processing circuitry configured to perform the processes discussed with respect to processor 310.

In general, programmer 104 comprises any suitable arrangement of hardware, alone or in combination with software and/or firmware, to perform the techniques attributed to programmer 104, and processor 310, user interface 302, and telemetry module 308 of programmer 104. In various examples, programmer 104 may include one or more processors, which may include fixed function processing circuitry and/or programmable processing circuitry, as formed by, for example, one or more microprocessors, DSPs, ASICs, FPGAs, or any other equivalent integrated or discrete logic circuitry, as well as any combinations of such components. Programmer 104 also, in various examples, may include a memory 311, such as RAM, ROM, PROM, EPROM, EEPROM, flash memory, a hard disk, a CD-ROM, comprising executable instructions for causing the one or more processors to perform the actions attributed to them. Moreover, although processor 310 and telemetry module 308 are described as separate modules, in some examples, processor 310 and telemetry module 308 may be functionally integrated with one another. In some examples, processor 310 and telemetry module 308 correspond to individual hardware units, such as ASICs, DSPs, FPGAs, or other hardware units.

Memory 311 (e.g., a storage device) may store instructions that, when executed by processor 310, cause processor 310 and programmer 104 to provide the functionality ascribed to programmer 104 throughout this disclosure. For example, memory 311 may include instructions that cause processor 310 to obtain a parameter set from memory, select a spatial electrode movement pattern, provide an interface that recommends or otherwise facilitates parameter value selection, or receive a user input and send a corresponding command to IMD 106, or instructions for any other functionality. In addition, memory 311 may include a plurality of programs, where each program includes a parameter set that defines stimulation therapy.

User interface 302 may include a button or keypad, lights, a speaker for voice commands, a display, such as a liquid crystal (LCD), light-emitting diode (LED), or organic light-emitting diode (OLED). In some examples the display may be a touch screen. User interface 302 may be configured to display any information related to the delivery of stimulation therapy, identified patient behaviors, sensed patient parameter values, patient behavior criteria, or any other such information. User interface 302 may also receive user input via user interface 302. The input may be, for example, in the form of pressing a button on a keypad or selecting an icon from a touch screen.

Telemetry module 308 may support wireless communication between IMD 106 and programmer 104 under the control of processor 310. Telemetry module 308 may also be configured to communicate with another computing device via wireless communication techniques, or direct communication through a wired connection. In some examples, telemetry module 308 provides wireless communication via an RF or proximal inductive medium. In some examples, telemetry module 308 includes an antenna, which may take on a variety of forms, such as an internal or external antenna. In some examples, IMD 106 and/or programmer 104 may communicate with remote servers via one or more cloud-services in order to deliver and/or receive information between a clinic and/or programmer.

Examples of local wireless communication techniques that may be employed to facilitate communication between programmer 104 and IMD 106 include RF communication according to the 802.11 or Bluetooth specification sets or other standard or proprietary telemetry protocols. In this manner, other external devices may be capable of communicating with programmer 104 without needing to establish a secure wireless connection. As described herein, telemetry module 308 may be configured to transmit a spatial electrode movement pattern or other stimulation parameter values to IMD 106 for delivery of stimulation therapy.

According to the techniques of the disclosure, in some examples, processor 310 of external programmer 104 defines the parameters of a homeostatic therapeutic window, stored in memory 311, for delivering DBS to patient 112. In one example, processor 311 of external programmer 104, via telemetry module 308, issues commands to IMD 106 causing IMD 106 to deliver electrical stimulation therapy via electrodes 116, 118 via leads 114. As noted above and in accordance with one or more techniques of this disclosure, external programmer 104 may issue commands to IMD 106 that cause IMD 106 to dynamically determine when to perform sensing and/or dynamically determine which electrodes to utilize for the sensing.

FIGS. 4A and 4B are conceptual diagrams of example leads 400 and 410, respectively, with respective electrodes carried by the lead. As shown in FIGS. 4A and 4B, leads 400 and 410 are examples of leads 114 shown in FIG. 1. As shown in FIG. 4A, lead 400 includes four electrode levels 404 (includes levels 404A-404D) mounted at various lengths of lead housing 402. Lead 400 is inserted into through cranium 122 to a target position within brain 18.

Lead 400 is implanted within brain 120 at a location determined by the clinician to be near an anatomical region to be stimulated. Electrode levels 404A, 404B, 404C, and 404D are equally spaced along the axial length of lead housing 30 at different axial positions. Each electrode level 404 may have one, two, three, or more electrodes located at different angular positions around the circumference (e.g., around the perimeter) of lead housing 402. As shown in FIG. 4A, electrode level 404A and 404D include a single respective ring electrode, and electrode levels 404B and 404C each include three electrodes at different circumferential positions. This electrode pattern may be referred to as a 1-3-3-1 lead in reference to the number of electrodes from the proximal end to the distal end of lead 400. Electrodes of one circumferential location may be lined up on an axis parallel to the longitudinal axis of lead 400. Alternatively, electrodes of different electrode levels may be staggered around the circumference of lead housing 402. In addition, lead 400 or 410 may include asymmetrical electrode locations around the circumference, or perimeter, of each lead or electrodes of the same level that have different sizes. These electrodes may include semi-circular electrodes that may or may not be circumferentially aligned between electrode levels.

Lead housing 402 may include a radiopaque stripe (not shown) along the outside of the lead housing. The radiopaque stripe corresponds to a certain circumferential location that allows lead 400 to the imaged when implanted in patient 112. Using the images of patient 112, the clinician can use the radiopaque stripe as a marker for the exact orientation of lead 400 within the brain of patient 112. Orientation of lead 400 may be needed to easily program the stimulation parameters by generating the correct electrode configuration to match the stimulation field defined by the clinician. In other examples, a marking mechanism other than a radiopaque stripe may be used to identify the orientation of lead 400. These marking mechanisms may include something similar to a tab, detent, or other structure on the outside of lead housing 402. In some examples, the clinician may note the position of markings along a lead wire during implantation to determine the orientation of lead 400 within patient 112. In some examples, programmer 104 may update the orientation of lead 400 in visualizations based on the movement of lead 400 from sensed signals.

FIG. 4B illustrates lead 410 that includes multiple electrodes at different respective circumferential positions at each of levels 414A-414D. Similar to lead 400, lead 410 is inserted through a burr hole in cranium 122 to a target location within brain 120. Lead 410 includes lead housing 412. Four electrode levels 414 (414A-414D) are located at the distal end of lead 410. Each electrode level 414 is evenly spaced from the adjacent electrode level and includes two or more electrodes. In one example, each electrode level 414 includes three, four, or more electrodes distributed around the circumference of lead housing 412. Each electrode may be substantially rectangular in shape. Alternatively, the individual electrodes may have alternative shapes, e.g., circular, oval, triangular, rounded rectangles, or the like.

In some examples, electrode levels 404 or 414 are not evenly spaced along the longitudinal axis of the respective leads 400 and 410. For example, electrode levels 404C and 404D may be spaced approximately 3 millimeters (mm) apart while electrodes 404A and 404B are 10 mm apart. Variable spaced electrode levels may be useful in reaching target anatomical regions deep within brain 120 while avoiding potentially undesirable anatomical regions. Further, the electrodes in adjacent levels need not be aligned in the direction as the longitudinal axis of the lead, and instead may be oriented diagonally with respect to the longitudinal axis.

Leads 400 and 410 are substantially rigid to prevent the implanted lead from varying from the expected lead shape. Leads 400 or 410 may be substantially cylindrical in shape. In other examples, leads 400 or 410 may be shaped differently than a cylinder. For example, the leads may include one or more curves to reach target anatomical regions of brain 18. In some examples, leads 400 or 410 may be similar to a flat paddle lead or a conformable lead shaped for patient 12. Also, in other examples, leads 400 and 410 may any of a variety of different polygonal cross sections (e.g., triangle, square, rectangle, octagonal, etc.) taken transverse to the longitudinal axis of the lead.

As shown in the example of lead 400, the plurality of electrodes of lead 400 includes a first set of three electrodes disposed at different respective positions around the longitudinal axis of the lead and at a first longitudinal position along the lead (e.g., electrode level 404B), a second set of three electrodes disposed at a second longitudinal position along the lead different than the first longitudinal position (e.g., electrode level 404C), and at least one ring electrode disposed at a third longitudinal position along the lead different than the first longitudinal position and the second longitudinal position (e.g., electrode level 404A and/or electrode level 404D). In some examples, electrode level 404D may be a bullet tip or cone shaped electrode that covers the distal end of lead 402.

Figure 5:
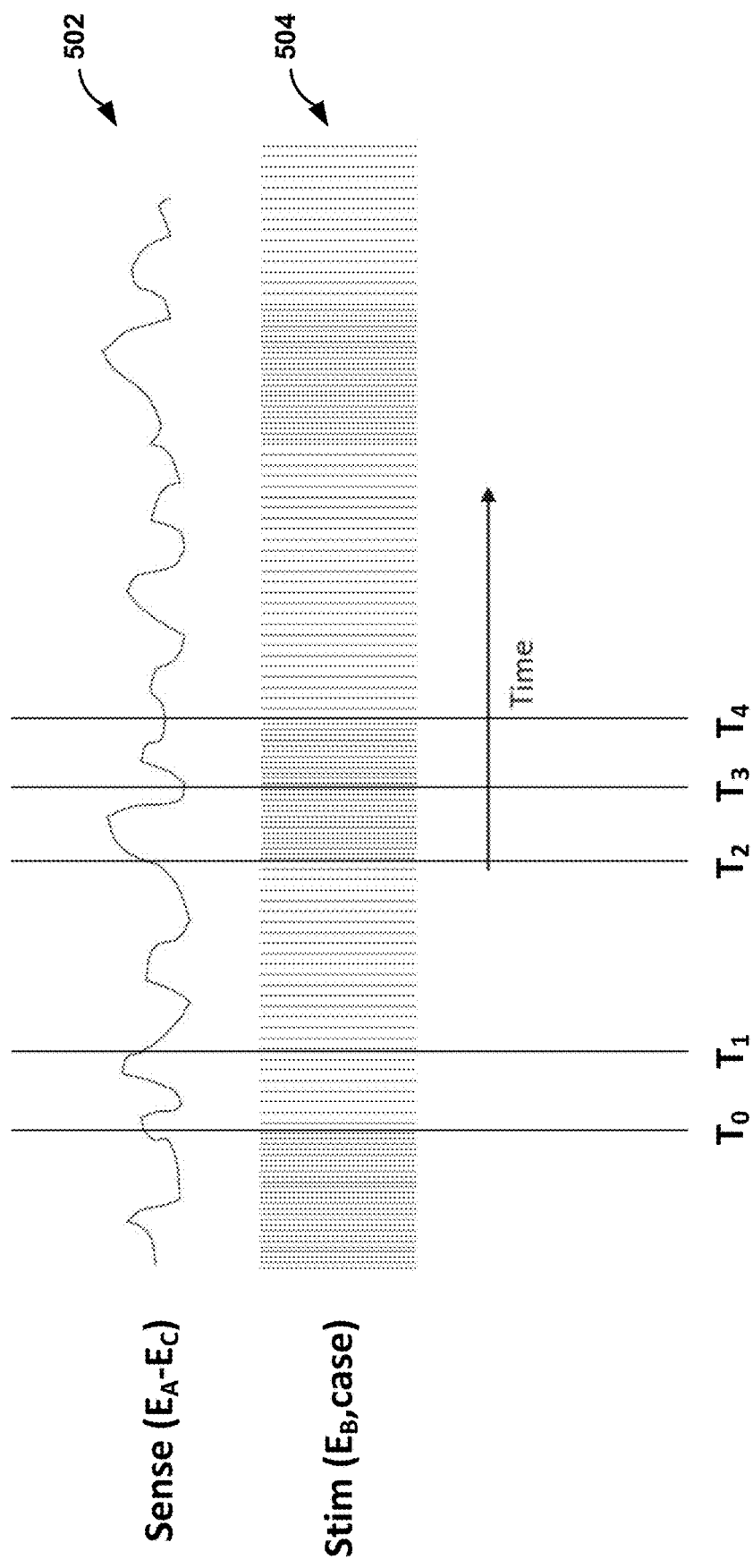
FIG. 5 is a graph illustrating an example of an electrical signal sensed contemporaneously with delivery of electrical stimulation, in accordance with one or more techniques of this disclosure.

FIG. 5 is a graph illustrating an example of an electrical signal sensed contemporaneously with delivery of electrical stimulation, in accordance with one or more techniques of this disclosure. As discussed above, IMD 106 may dynamically select electrodes to use for sensing of electrical signals. For instance, responsive to determining to deliver electrical stimulation via an electrode $E_B$ (e.g., corresponding to an electrode at position B of an electrode of electrodes 116), IMD 106 may determine to perform sensing via a pair of electrodes of the plurality of electrodes that are symmetrically distributed across the determined electrode (e.g., electrodes $E_A$ and $E_C$). Plot 502 may include data representing electrical signals sensed across electrodes $E_A$ and $E_C$, and plot 504 may include data representing pulses delivered via electrode $E_B$ and a case electrode (e.g., monopolar stimulation). In this way, IMD 106 may stream sensed electrical signals via one channel of LFP while stimulation is active.

As also discussed above, in some examples, IMD 106 may mark some data as viable and may mark some data as non-viable. For instance, IMD 106 may wait a specified period of time after adjustment of stimulation delivery until commencing to sense electrical signals (and/or mark electrical signals measured prior to an end of the specified period as non-viable and mark electrical signals measured after the end of the specified period as viable). In the example of FIG. 5, IMD 106 may adjust stimulation delivery at time $T_0$ (e.g., reduce a pulse frequency), mark data representing electrical signals sensed between $T_0$ and $T_1$ as non-viable, and mark data representing electrical signals sensed between $T_1$ and $T_2$ as viable. The time between $T_0$ and $T_1$ may be the specified period. As shown in FIG. 5, IMD 106 may again adjust stimulation delivery at time $T_2$ (e.g., increase a pulse frequency), mark data representing electrical signals sensed between $T_2$ and $T_3$ as non-viable, and mark data representing electrical signals sensed between $T_3$ and $T_4$ as viable. The time between $T_2$ and $T_3$ may be the specified period.

Figure 6:
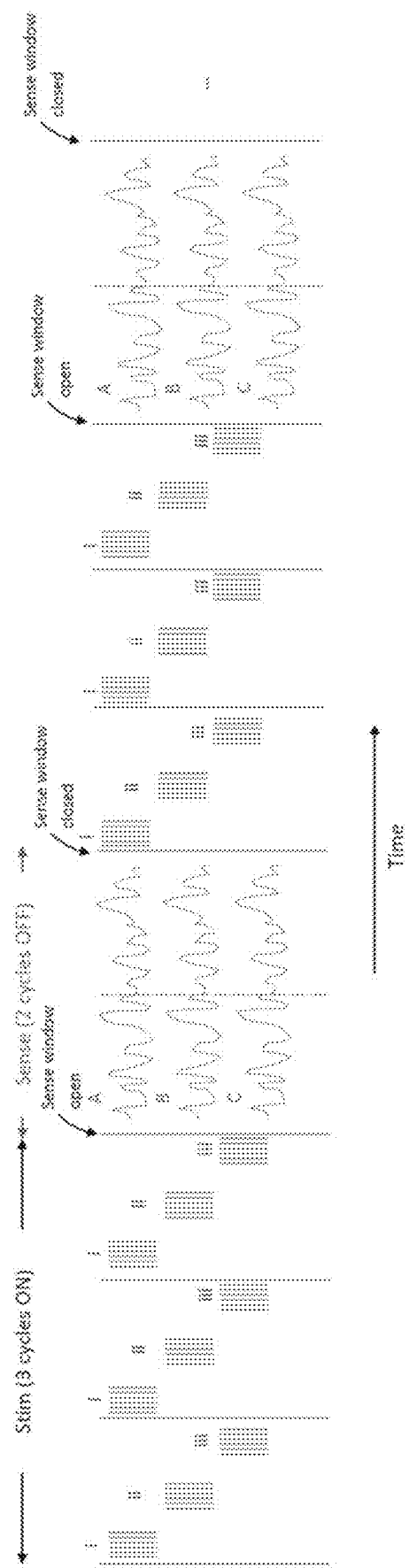
FIG. 6 is a timing diagram illustrating an example combination of stimulation and sensing, in accordance with one or more techniques of this disclosure.

FIG. 6 is a timing diagram illustrating an example combination of stimulation and sensing, in accordance with one or more techniques of this disclosure. In the example of FIG. 6, IMD 106 may operate under a paradigm of cycles (e.g., frames). Cycles may be sensing cycles, stimulation cycles, or hybrid sensing/simulation cycles. As shown in FIG. 6, IMD 106 may perform three stimulation cycles followed by two sensing cycles.

In each of the example stimulation cycles, IMD 106 may stimulate via one or more electrodes. For instance, as shown in FIG. 6, in each of the stimulation cycles, IMD 106 may stimulate, successively, via a first electrode (i), a second electrode (ii), and a third electrode (iii).

IMD 106 may accomplish stimulation via the first electrode (i) by delivering monopolar stimulation between an electrode $E_B$ and a case electrode of IMD 106. IMD 106 may accomplish stimulation via the second electrode (ii) by delivering monopolar stimulation between an electrode $E_C$ and a case electrode of IMD 106. IMD 106 may accomplish stimulation via the third electrode (iii) by delivering monopolar stimulation between an electrode $E_D$ and a case electrode of IMD 106.

In each of the example sensing cycles, IMD 106 may sense electrical signals via one or more electrodes. For instance, as shown in FIG. 6, in each of the sensing cycles, IMD 106 may stimulate, concurrently, via a first pair of electrodes (A), a second pair of electrodes (B), and a third pair of electrodes (C).

IMD 106 may accomplish sensing via the first pair of electrodes (A) by sensing electrical signals (e.g., voltage across) between electrode $E_A$ and $E_C$. IMD 106 may accomplish sensing via the second pair of electrodes (B) by sensing electrical signals (e.g., voltage across) between electrode $E_B$ and $E_D$. IMD 106 may accomplish sensing via the third pair of electrodes (B) by sensing electrical signals (e.g., voltage across) between electrode $E_C$ and $E_E$.

Hybrid sensing/stimulation cycles may have various attributes. As one example, hybrid cycles may be particularly compatible with static electrode patterns. As another example, when sensing during a hybrid cycle, IMD 106 may stream data from one bipolar pair per lead with stimulation on. As another example, data sensed during hybrid cycles may be confounded by frequency shifts in stimulation patterns (e.g., artifacts).

Sensing cycles may have various attributes. As one example, sensing cycles may be particularly compatible with electrode switching patterns. As another example, when sensing during a sensing cycle, IMD 106 may stream data from multiple (e.g., 3) bipolar pairs per lead with stimulation off. As another example, sensing cycles can be scheduled/interleaved with stimulation cycles or hybrid cycles within a pattern. As another example, sensing cycles can be performed after stimulation has been manually paused (e.g., as discussed with reference to FIGS. 8A and 8B).

Figure 7:
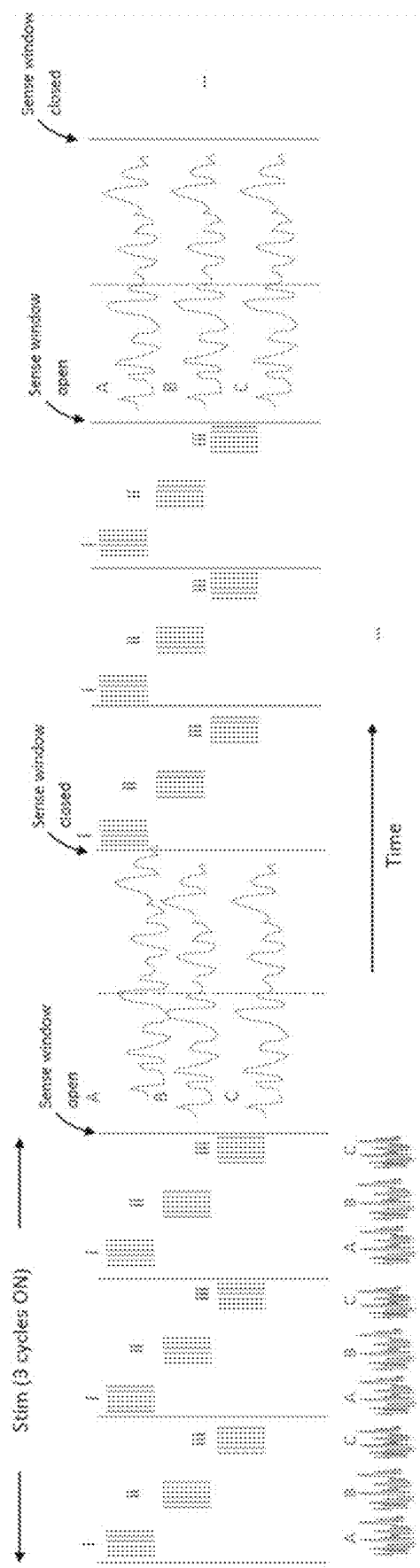
FIG. 7 is a timing diagram illustrating an example combination of stimulation and sensing, in accordance with one or more techniques of this disclosure.

FIG. 7 is a timing diagram illustrating an example combination of stimulation and sensing, in accordance with one or more techniques of this disclosure. In the example of FIG. 7, IMD 106 may operate under a paradigm of cycles (e.g., frames). Cycles may be sensing cycles, stimulation cycles, or hybrid sensing/simulation cycles. As shown in FIG. 7, IMD 106 may perform three hybrid sensing/stimulation cycles followed by two sensing cycles. The electrode definitions of FIG. 7 may be the same as those discussed above for FIG. 6.

As can be seen in FIG. 7, during the hybrid sensing/stimulation cycles, IMD 106 may dynamically adjust which electrodes as being used for sensing based on the electrode being used to deliver stimulation. For instance, when IMD 106 is delivering stimulation via first electrode (i), IMD 106 may perform sensing via first pair of electrodes (A) (e.g., sense electrical signals via electrodes symmetrically displaced about the current stimulation electrode). Then, when IMD 106 switches from delivering stimulation via the first electrode (i) to delivering stimulation via second electrode (ii), IMD 106 may switch to sense electrical signals via second pair of electrodes (B).

Figure 8A:
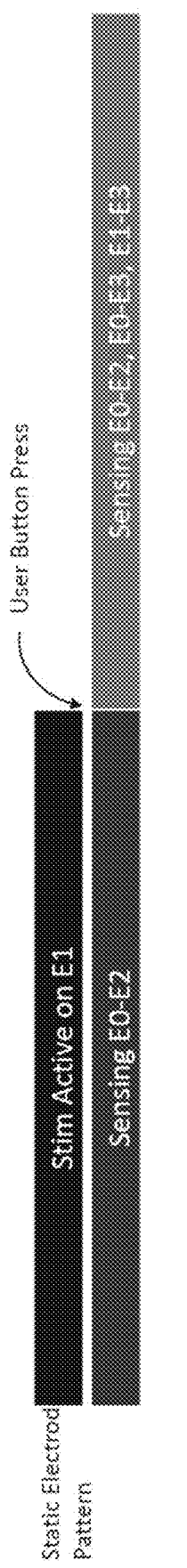
FIGS. 8A and 8B are timing diagrams illustrating example of user-controlled toggling between cycles, in accordance with one or more techniques of this disclosure.
Figure 8B:
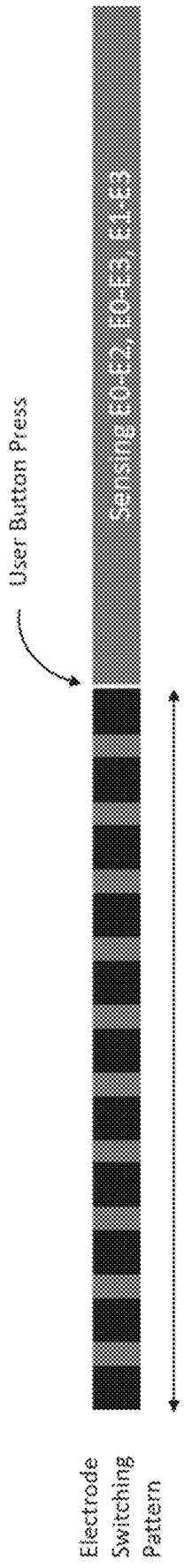

FIGS. 8A and 8B are timing diagrams illustrating example of user-controlled toggling between cycles, in accordance with one or more techniques of this disclosure. As shown in FIG. 8A, IMD 106 may receive user input that causes IMD 106 to switch from a hybrid sensing/stimulation cycle to a sensing cycle. As shown in FIG. 8B, IMD 106 may receive user input that causes IMD 106 to switch from alternating stimulation and sensing cycles to a sensing cycle. IMD 106 may receive the user input using any suitable means. As one example, IMD 106 may receive the user input via a button, such as a button on external programmer 104.

Figure 9:
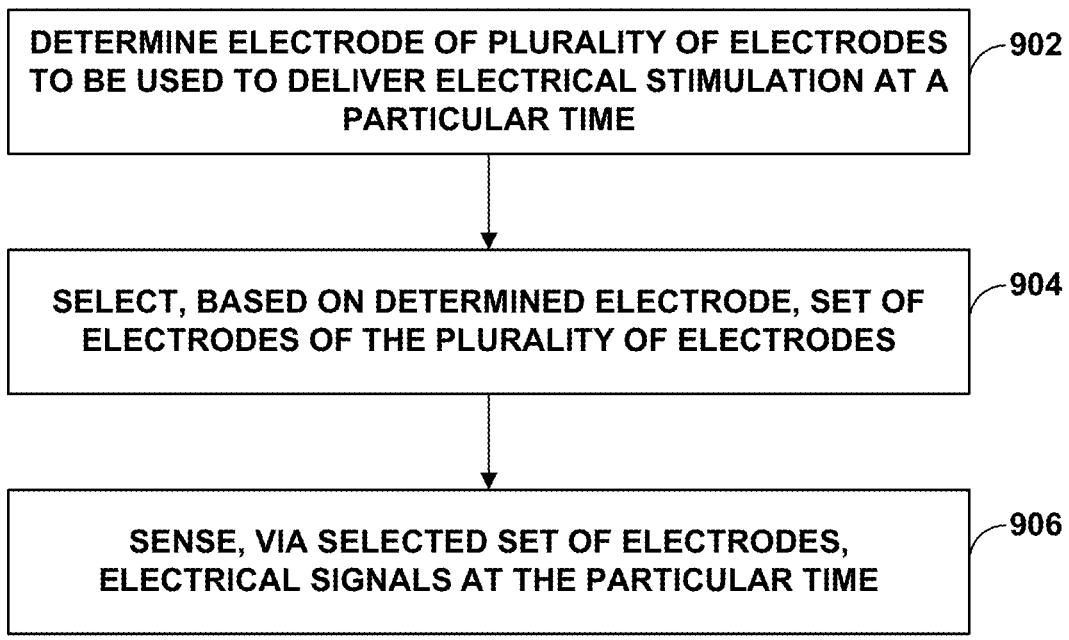
FIG. 9 is a flowchart illustrating an example technique for dynamic sensing of electrical signals, in accordance with one or more techniques of this disclosure.

FIG. 9 is a flowchart illustrating an example technique for dynamic sensing of electrical signals, in accordance with one or more techniques of this disclosure. For purposes of explanation, the technique of FIG. 9 is described as being performed by IMD 106. However, the technique of FIG. 9 may be performed other devices.

IMD 106 may determine an electrode of a plurality of electrodes of a lead to be used to deliver electrical stimulation to a patient at a particular time (902). For instance, IMD 106 may determine to deliver electrical stimulation via electrode $E_B$ and a case electrode of IMD 106.

IMD 106 may select, based on the determined electrode, a set of electrodes of the plurality of electrodes (904). For instance, IMD 106 may select, as the set of electrodes, a pair of electrodes of the plurality of electrodes that are symmetrically distributed across the determined electrode. In particular, where the determined electrode is electrode $E_B$, IMD 106 may select electrodes $E_A$ and $E_C$ as the set of electrodes.

IMD 106 may sense, via the selected set of electrodes, electrical signals of the patient at the particular time (906). For instance, at the particular time, IMD 106 may deliver monopolar electrical stimulation via the electrode and a case electrode of the IMD while also sensing electrical signals of the patient via the selected set of electrodes. As discussed above with reference to FIG. 5, IMD 106 may deliver electrical stimulation via electrode $E_B$ and a case electrode of IMD 106 and sense via electrodes $E_A$ and $E_C$.

As discussed above, in some examples, IMD 106 may also sense via the set of electrodes during a sense window that does not include the particular time. The sense window may be formed of one or more sense cycles/frames.

IMD 106 may tag the sense electrical signals. As one example, IMD 106 may tag data representing electrical signals sensed during stimulation cycles (e.g., data sensed during hybrid cycles) as being sensed during delivery of stimulation. As another example, IMD 106 may tag data representing electrical signals sensed during sensing cycles as being sensed during the sense window.

IMD 106 may perform one or more actions based on the sensed electrical signals. For instance, IMD 106 may adjust, based on the sensed electrical signals, delivery of electrical stimulation to the patient. In this way, IMD 106 may perform closed-loop stimulation.

The following examples may illustrate one or more examples of our disclosure:

Example 1

A method comprising: determining, by an implantable medical device (IMD), an electrode of a plurality of electrodes of a lead to be used to deliver electrical stimulation to a patient at a particular time; selecting, by the IMD and based on the determined electrode, a set of electrodes of the plurality of electrodes; and sensing, by the IMD and via the selected set of electrodes, electrical signals of the patient at the particular time.

Example 2

The method of example 1, further comprising: delivering, by the IMD and at the particular time, monopolar electrical stimulation via the electrode and a case electrode of the IMD.

Example 3

The method of example 1 or example 2, wherein sensing the electrical signals comprises: sensing, via the selected set of electrodes, first electrical signals at the particular time; and sensing, via the selected set of electrodes, second electrical signals during a sense window that does not include the particular time.

Example 4

The method of example 3, further comprising: tagging, by the IMD, data representing the first electrical signals as being sensed during delivery of stimulation; and tagging, by the IMD, data representing the second electrical signals as being sensed during the sense window.

Example 5

The method of any of the preceding examples, wherein selecting the set of electrodes comprises: selecting, as the set of electrodes, a pair of electrodes of the plurality of electrodes that are symmetrically distributed across the determined electrode.

Example 6

The method of any of the preceding examples, further comprising: determining an amplitude of the electrical stimulation; and adjusting a delay of a sense window based on the determined amplitude.

Example 7

The method of any of the preceding examples, wherein the particular time is a first time, the determined electrode is a first determined electrode, the set of electrodes is a first set of electrodes, the method further comprising: determining, by the IMD, a second electrode of the plurality of electrodes of the lead to be used to deliver electrical stimulation to the patient at a second time that is different than the first time; selecting, by the IMD and based on the second determined electrode, a second set of electrodes of the plurality of electrodes; and sensing, by the IMD and via the selected second set of electrodes, electrical signals of the patient at the second time.

Example 8

The method of any of the preceding examples, further comprising: adjusting, based on the sensed electrical signals, delivery of electrical stimulation to the patient.

Example 9

A system comprising: a memory; and processing circuitry configured to perform the method of any of examples 1-8.

Example 10

A computer-readable storage medium comprising instructions that, when executed, cause processing circuitry to perform the method any of examples 1-8.

There may be certain changes in patient or disease state that result in a change of sensing modality being employed by the system. These patient state changes could be driven by biochemical, electrophysical, activity, and postural, or other changes. In these cases, the optimization of neural sensing parameters for a given current sensing modality may not yield the ideal device behavior or patient treatment (i.e., a different biomarker that is acquired via a different sensing modality may provide better insight into the patient state, how to adapt therapy, etc.). Therefore, in addition to or in place of the optimization of any given specific sensing modality, a higher-level sensing modality optimization/priority scheme could be employed to further enhance the device's ability to acquire the most relevant biomarker at any given time.

The techniques described in this disclosure may be implemented, at least in part, in hardware, software, firmware or any combination thereof. For example, various aspects of the described techniques may be implemented within one or more processors, such as fixed function processing circuitry and/or programmable processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method comprising:
   determining, by an implantable medical device (IMD), an electrode of a plurality of electrodes of a lead to be used to deliver electrical stimulation to a patient at a particular time;
   selecting, by the IMD and based on the determined electrode, a set of electrodes of the plurality of electrodes;
   sensing, by the IMD and via the selected set of electrodes, electrical signals of the patient at the particular time, wherein sensing the electrical signals comprises:
   sensing, via the selected set of electrodes, first electrical signals at the particular time; and
   sensing, via the selected set of electrodes, second electrical signals during a sense window that does not include the particular time;
   determining an amplitude of the electrical stimulation; and
   adjusting a delay of the sense window based on the determined amplitude, the delay representing an amount of time between when the electrical stimulation was delivered and when the sense window opens.

2. The method of claim 1, further comprising:
   delivering, by the IMD and at the particular time, monopolar electrical stimulation via the electrode and a case electrode of the IMD.

3. The method of claim 1, further comprising:
   tagging, by the IMD, data representing the first electrical signals as being sensed during delivery of stimulation; and tagging, by the IMD, data representing the second electrical signals as being sensed during the sense window.

4. The method of claim 1, wherein selecting the set of electrodes comprises:
selecting, as the set of electrodes, a pair of electrodes of the plurality of electrodes that are symmetrically distributed across the determined electrode.

5. The method of claim 1, wherein the particular time is a first time, the determined electrode is a first determined electrode, the set of electrodes is a first set of electrodes, the method further comprising:
determining, by the IMD, a second electrode of the plurality of electrodes of the lead to be used to deliver electrical stimulation to the patient at a second time that is different than the first time;
selecting, by the IMD and based on the second determined electrode, a second set of electrodes of the plurality of electrodes; and
sensing, by the IMD and via the selected second set of electrodes, electrical signals of the patient at the second time.

6. The method of claim 1, further comprising:
adjusting, based on the sensed electrical signals, delivery of electrical stimulation to the patient.

7. A system comprising:
a memory; and
processing circuitry configured to:
determine, an electrode of a plurality of electrodes of a lead to be used to deliver electrical stimulation to a patient at a particular time;
select, based on the determined electrode, a set of electrodes of the plurality of electrodes;
determine an amplitude of the electrical stimulation;
adjust a delay of a sense window based on the amplitude, the delay representing an amount of time between when the electrical stimulation is delivered and when the sense window opens; and
sense, via the selected set of electrodes, electrical signals of the patient during the sense window.

8. The system of claim 7, further comprising:
an implantable medical device (IMD),
wherein the processing circuitry is configured to cause the IMD to deliver, at the particular time, monopolar electrical stimulation via the electrode and a case electrode of the IMD.

9. The system of claim 7, wherein, to sense the electrical signals, the processing circuitry is configured to:
sense, via the selected set of electrodes, first electrical signals at the particular time; and
sense, via the selected set of electrodes, second electrical signals during the sense window.

10. The system of claim 9, wherein the processing circuitry is further configured to:
tag data representing the first electrical signals as being sensed during delivery of stimulation; and
tag data representing the second electrical signals as being sensed during the sense window.

11. The system of claim 7, wherein, to select the set of electrodes, the processing circuitry is configured to:
select, as the set of electrodes, a pair of electrodes of the plurality of electrodes that are symmetrically distributed across the determined electrode.

12. The system of claim 7, wherein the particular time is a first time, the determined electrode is a first determined electrode, the set of electrodes is a first set of electrodes, and wherein the processing circuitry is further configured to:
determine a second electrode of the plurality of electrodes of the lead to be used to deliver electrical stimulation to the patient at a second time that is different than the first time;
select, based on the second determined electrode, a second set of electrodes of the plurality of electrodes; and
sense, via the selected second set of electrodes, electrical signals of the patient at the second time.

13. The system of claim 7, wherein the processing circuitry is further configured to:
adjust, based on the sensed electrical signals, delivery of electrical stimulation to the patient.

14. A non-transitory computer readable storage medium comprising instructions that, when executed, cause processing circuitry to:
determine an electrode of a plurality of electrodes of a lead to be used to deliver electrical stimulation to a patient at a particular time;
select, based on the determined electrode, a set of electrodes of the plurality of electrodes;
sense, via the selected set of electrodes, electrical signals of the patient at the particular time, wherein the instructions that cause the processing circuitry to sense the electrical signals comprise instructions that cause the processing circuitry to:
sense, via the selected set of electrodes, first electrical signals at the particular time; and
sense, via the selected set of electrodes, second electrical signals during a sense window that does not include the particular time; and
determine an amplitude of the electrical stimulation; and
adjust a delay of the sense window based on the determined amplitude, the delay representing an amount of time between when the electrical stimulation was delivered and when the sense window opens.

15. A non-transitory computer readable storage medium of claim 14, further comprising instructions that cause the processing circuitry to:
tag data representing the first electrical signals as being sensed during delivery of stimulation; and
tag data representing the second electrical signals as being sensed during the sense window.

16. A non-transitory computer readable storage medium of claim 14, wherein the instructions that cause the processing circuitry to select the set of electrodes comprise instructions that cause the processing circuitry to:
select, as the set of electrodes, a pair of electrodes of the plurality of electrodes that are symmetrically distributed across the determined electrode.

* * * * *